United States Patent [19]
Haslwanter et al.

[11] Patent Number: 5,854,269
[45] Date of Patent: Dec. 29, 1998

[54] NASAL SPRAY COMPOSITIONS

[75] Inventors: Joseph A. Haslwanter, Germantown; William Rencher, Cordova, both of Tenn.

[73] Assignee: Schering-Plough Healthcare Products, Inc., Kenilworth, N.J.

[21] Appl. No.: 640,767

[22] PCT Filed: Nov. 17, 1994

[86] PCT No.: PCT/US94/12945

§ 371 Date: Aug. 5, 1996

§ 102(e) Date: Aug. 5, 1996

[87] PCT Pub. No.: WO95/13810

PCT Pub. Date: May 26, 1995

[51] Int. Cl.⁶ .................................................. A61K 31/355
[52] U.S. Cl. ............................................................. 514/385
[58] Field of Search ............................................... 514/385

[56] References Cited

U.S. PATENT DOCUMENTS 5,114,979   5/1992   Kielley ..................................... 514/783

*Primary Examiner*—Zohreh Fay
*Attorney, Agent, or Firm*—Arthur Mann; John J. Maitner

[57] ABSTRACT

An aqueous nasal decongestant composition containing oxymatazoline is disclosed which does not contain mercurial preservatives.

8 Claims, No Drawings

NASAL SPRAY COMPOSITIONS

BACKGROUND OF THE INVENTION

This invention relates to an aqueous, topical, nasal decongestant composition containing oxymetazoline or a pharmaceutically acceptable salt thereof, an aqueous carrier which does not require undesirable mercurial anti-microbal agents.

Aqueous, topical, nasal decongestant compositions containing oxymetazoline hydrochloride, the longest acting nasal decongestant currently available, are applied to the nasal passages of mammals especially human beings to effect temporary relief of nasal congestion associated with colds, hay fever and sinusitis.

It is known that one of the most common complaints of patients and consumers that use nasal spray products is the drying and associated stinging within the nasal cavity. Other common nasal product negative attributes include odor and product taste. Additionally, due to the propensity of nasal products to become microbially contaminated, the use of a two preservative ingredient formulation is preferred.

It is also well known that aromatic ingredients, such as menthol, camphor and eucalyptol are used to promote the opening, draining and subsequent relief of sinus pressure in nasal spray products. Unfortunately, such ingredients are not soluble in water and require the addition of solubilizers to the formulation. It is also unfortunate that the required amount and solubilizers, such as Polysorbate 80 and alcohol solvents significantly adds to the associated unpleasant odor and stinging within the nasal cavity. It is also well known that the addition of surfactants, such as Polysorbate 80 greatly reduces the antimicrobial activity of benzalkonium chloride. As a result of this microbial activity reduction in benzalkonium chloride, other well known mercurial preservatives, such as thimerosal and phenyl mercuric acetate are reluctantly used.

A menthol flavored composition containing vapors of menthol, eucalyptol and camphor in addition to oxymetazoline hydrochloride and an aqueous carrier is currently available as an OTC product under the tradename AFRIN® Menthol Nasal Spray from Schering-Plough HealthCare Products, Liberty Corner, N.J. The aqueous carrier of this product contains benzalkonium chloride, glycerine, phenylmercuric acetate, sorbitol, polysorbate 80 and water.

The use of mercurial preservatives, e.g. phenylmercuric acetate, in nasal compositions, has been questioned and elimination of mercurial preservatives is desirable.

We have surprisingly discovered that incorporation of an aromatic alcohol, e.g. benzyl alcohol and phenyl ethyl alcohol, in menthol type nasal sprays containing oxymetazoline allows removal of the undesirable mercurial preservatives from the nasal spray compositions.

It has been discovered that the incorporation of benzyl alcohol in menthol type aromatic nasal sprays has generated benefits beyond what would be normally expected as "well known" within the formulation arts. It has been found that the characteristic odor of the aromatic alcohols is effectively covered by the menthol type odor. This resulted in the development of a product with a pleasant aromatic odor. It has also been discovered that the addition of aromatic alcohols allowed for the unexpected and desired reduction, and or elimination of required surfactants. As surfactants are also characterized as having an unpleasant odor this reduction cointributed to a pleasant product odor. Furthermore, it has been unexpectedly discovered that the lower surfactant usage levels did not affect the microbial activity of benzalkonium chloride, allowing removal of mercurial preservatives and still maintain a preservative system based on two ingredients.

SUMMARY OF THE INVENTION

The present invention provides an aqueous, topical nasal, decongestant composition comprising an amount of oxymetazoline or a pharmaceutically acceptable salt thereof sufficient to effect nasal decongestion and an aqueous carrier which is free of mercurial preservatives.

The present invention also provides an aqueous, flavored, topical nasal decongestant composition comprising an amount of oxymetazoline or a pharmaceutically acceptable salt thereof sufficient to effect nasal decongestion and an aqueous carrier comprising:

70 to 90% by weight/volume of water;

0.10 to 5.00% by weight/volume of an aromatic alcohol;

0 to 0.3% by weight/volume of a non-mercurial antimicrobial preservative 0 to 10% by weight/volume of a moisturizing agent;

0 to 0.10% by weight/volume of an antioxidant;

0 to 2.00% by weight/volume of a surfactant;

0 to 0.75% by weight/volume of menthol;

0 to 0.15% by weight/volume of camphor;

0 to 0.15% by weight/volume of eucalyptol; and a sufficient amount of a pharmaceutically acceptable buffer to maintain the pH of the composition within the range of about 4.00–8.00;

and QS water.

The present invention further provides a method of treating nasal congestion by administering to a nasal passage of a patient with nasal congestion an aqueous, topical nasal decongestant composition of the present invention.

DETAILED DESCRIPTION OF THE INVENTION

The novel nasal compositions of the present invention contain oxymetazoline and an aqueous carrier.

The amount of oxymetazoline or pharmaceutically acceptable salt thereof found sufficient to effect nasal decongestion is in the range of about 0.01% to about 0.1% by weight/volume of the topical nasal decongestant composition. Typically, 0.05% by weight/volume of oxymetazoline (as the HCl salt) is suitable for adults and children above five years of age. Oxymetazoline HCl is commercially available from Schering Labs. Kenilworth, N.J. See also The Merck Index. Tenth Edition, 1983 p. 6838. By the term "pharmaceutically acceptable salt" as used herein is meant the acid addition salt formed by admixing oxymetazoline with a pharmaceutically acceptable acid such as HCl, HF, $H_2SO_4$, $HNO_3$, malonic, succinic, trifluoroacetic acids and the like.

The compositions of the present invention contain an aromatic alcohol selected from the group consisting of benzyl alcohol and phenyl ethyl alcohol. The amount of aromatic alcohol present in the composition is from about 0.10 to 5.00% by weight/volume of the total composition. Ranges of 0.20–3.00% by weight/volume of the total composition are particularly suitable, and a range of 0.25 to 1.00% by weight/volume of the total composition being most preferable.

The compositions of the present invention may contain a surfactant, e.g. polysorbate 80. The amount of surfactant present in the composition is from about 0 to 2.00% by weight/volume of the total composition. Ranges of 0 to 1.50% by weight/volume of the total composition are particularly suitable, and a range of 0 to 1.25% by weight/volume of the total composition being most preferable.

The compositions of the present invention may contain moisturizing agents, e.g. propylene glycol. The amount of moisturizing agent present in the composition is from about 0 to 10.00% by weight/volume of the total composition. Ranges of 1.00 to 4.00% by weight/volume of the total composition are particularly suitable, and a range of 1.5 to 3.50% by weight/volume of the total composition being most preferable.

The compositions of the present invention may contain an antioxidant, e.g. disodium EDTA. The amount of antioxidant present in the composition is from about 0 to 0.10% by weight/volume of the total composition. Ranges of 0.01 to 0.05% by weight/volume of the total composition are particularly suitable, and a range of 0.015 to 0.030% by weight/volume of the total composition being most preferable.

The compositions of the present invention contains at least one antimicrobial preservative in the range of 0.01% to about 0.3% by weight/volume of the composition. Typical suitable preservatives function as antimicrobial agents and include the commercially available preservatives, e.g. benzalkonium chloride in the range of about 0.02 to about 0.025% by weight/volume.

The compositions of the present invention also include pharmaceutically acceptable buffers sufficient to adjust and maintain the pH of the compositions of the present invention in the range of about 4.0 to about 8.0, preferably about 5.5 to about 7.0 and 6.25 to 6.75 being most preferable. Typically suitable buffers include citrate, phosphate and glycine.

The nasal spray compositions of the present invention is manufactured in a conventional manner by thoroughly mixing the ingredients at ambient or elevated temperatures in order to achieve solubility of ingredients where appropriate.

All percentages are by weight/volume. The definitions of components whose chemical composition is not immediately clear from the name used, such as "Polysorbate 80", may be found in the CTFA Cosmetic Ingredients Dictionary, 4th Edition, 1991, published by Cosmetic Toiletry and Fragrance Association, Inc., Washington, DC.

The following examples describe in detail the invention. It will be apparent to those skilled in the art that modifications may be practiced without departing from the purpose and intent of this disclosure.

EXAMPLE 1

An aromatic nasal spray formulated with 2.2% solubilizing agent requiring a preservative system based on mercurial compounds to yield satisfactory microbial activity.

| Ingredients | % Wt/Vol |
| --- | --- |
| Water USP purified | 80.0000 |
| Sorbitol (70% solution) | 5.7100 |
| Glycine USP (aminoacetic acid) | 0.3747 |
| Benzalkonium chloride (17% solution) | 0.1169 |
| Polysorbate 80 NF (Tween 80) | 2.2000 |
| L-Menthol USP | 0.2000 |
| Camphor USP (synthetic) | 0.0400 |
| Eucalyptol | 0.0400 |
| Phenylmercuric Acetate | 0.0024 |
| Oxymetazoline Hydrochloride USP | 0.0500 |
| Water USP purified | QS |

EXAMPLE 2

A satisfactorily preserved mercurial free aromatic nasal spray is formulated with 1.0% Benzyl alcohol enabling a 43.2% reduction in solubilizing agent.

| Ingredients | % Wt/Vol |
| --- | --- |
| Water USP purified | 80.0000 |
| Sodium phosphate monobasic | 0.5525 |
| Sodium phosphate dibasic | 0.0975 |
| Disodium EDTA | 0.0200 |
| Benzyl alcohol | 1.0000 |
| Benzalkonium chloride (17% solution) | 0.1177 |
| Propylene glycol USP | 3.5000 |
| Polysorbate 80 NF (Tween 80) | 1.2500 |
| L-Menthol USP | 0.1750 |
| Camphor USP (Synthetic) | 0.0300 |
| Eucalyptol | 0.0300 |
| Oxymetazoline hydrochloride USP | 0.0500 |
| Water USP purified | QS |

Method of Preparation

1. To any appropriate reaction container, add the following: sodium phosphate monobasic, sodium phosphate dibasic, disodium EDTA, benzyl alcohol and oxymetazoline hydrochloride to 70% of the water at a temperature of 50° C. Continue mixing the aqueous mixture while cooling to 30° C.

2. In a separate container, add with mixing the following: menthol, camphor, eucalyptol and Polysorbate 80 and continue to mix until all is in solution.

3. In a separate container, add 10% of the water and the propylene glycol and mix the solution at 30° C. for at least 5 minutes.

4. Transfer the solution of step 2 to the solution of step 3 and mix for at least 5 minutes.

5. Transfer the contents of step 4 into the aqueous mixture of step 1.

6. While mixing, add the benzalkonium chloride 17% solution to the aqueous mixture of step 5 and mix for at least 5 minutes.

7. Adjust the final batch volume with water, mix until uniform and then filter.

EXAMPLE 3

A satisfactorily preserved mercurial free aromatic nasal spray is formulated with 0.25% Benzyl alcohol enabling a 90.9% reduction in solubilizing agent.

| Ingredients | % Wt/Vol |
| --- | --- |
| Water USP purified | 80.0000 |
| Sodium phosphate monobasic | 0.5525 |
| Sodium phosphate dibasic | 0.0975 |
| Disodium EDTA | 0.0200 |
| Benzyl alcohol | 0.2500 |
| Benzalkonium chloride (17% solution) | 0.1177 |
| Propylene glycol USP | 1.5000 |
| Polysorbate 80 (Tween 80) | 0.1500 |
| L-Menthol USP | 0.0900 |
| Camphor USP (Synthetic) | 0.0300 |
| Eucalyptol | 0.0300 |
| Oxymetazoline hydrochloride | 0.0500 |
| Water USP purified | QS |

The procedure for preparation of this composition is as described in Example 2.

EXAMPLE 4

A satisfactorily preserved mercurial free aromatic nasal spray is formulated with 0.25% Benzyl alcohol enabling a 93.2% reduction in solubilizing agent.

| Ingredients | % Wt/Vol |
| --- | --- |
| Water USP purified | 80.0000 |
| Sodium phosphate monobasic | 0.5525 |
| Sodium phosphate dibasic | 0.0975 |
| Disodium EDTA | 0.0200 |
| Benzyl alcohol | 0.2500 |
| Benzalkonium chloride (17% solution) | 0.1177 |
| Propylene glycol USP | 1.5000 |
| Polysorbate 80 (Tween 80) | 0.1500 |
| L-Menthol USP | 0.0400 |
| Camphor USP (Synthetic) | 0.0100 |
| Eucalyptol | 0.0100 |
| Oxymetazoline hydrochloride | 0.0500 |
| Water USP purified | QS |

The procedure for preparation of this composition is as described in Example 2.

EXAMPLE 5

A satisfactorily preserved mercurial free aromatic nasal spray is formulated with 0.25% Benzyl alcohol and reduced aromatic ingredients enabling a 100.0% reduction in solubilizing agent.

| Ingredients | % Wt/Vol |
| --- | --- |
| Water USP purified | 80.0000 |
| Sodium phosphate monobasic | 0.5525 |
| Sodium phosphate dibasic | 0.0975 |
| Disodium EDTA | 0.0200 |
| Benzyl alcohol | 0.2500 |
| Benzalkonium chloride (17% solution) | 0.1177 |
| Propylene glycol USP | 1.5000 |
| Eucalyptol | 0.0300 |
| Oxymetazoline hydrochloride | 0.0500 |
| Water USP purified | QS |

The procedure for preparation of this composition is as described in Example 2.

We claim:

1. An aqueous, topical, nasal decongestant composition comprising an amount of oxymetazoline or a pharmaceutically acceptable salt thereof sufficient to effect nasal decongestion and an aqueous carrier comprising:

70 to 90% by weight/volume of water;

0.10 to 5.00% by weight/volume of an aromatic alcohol;

0.01 to 0.3% by weight/volume of a non-mercurial antimicrobial preservative;

0 to 10% by weight/volume of a moisturizing agent;

0 to 0.10% by weight/volume of an antioxidant;

0 to 2.00% by weight/volume of a surfactant;

0 to 0.75% by weight/volume of menthol;

0 to 0.15% by weight/volume of camphor;

0 to 0.15% by weight/volume of eucalyptol;

a sufficient amount of a pharmaceutically acceptable buffer to maintain the pH of the composition within the range of about 4.00 to 8.00; and QS water, said composition being free of mercurial antimicrobial preservatives.

2. The composition of claim 1 comprising:

0.05% by weight/volume of oxymetazoline;

80% by weight/volume of water;

0.25–1.00% by weight/volume of an aromatic alcohol;

0.02 to 0.025% by weight/volume of a non-mercurial antimicrobial preservative;

1.5 to 3.5% by weight/volume of a moisturizing agent;

0.015 to 0.03% by weight/volume of an antioxidant;

0.0 to 1.25% by weight/volume of a surfactant;

0.10 to 0.20% by weight/volume of menthol;

0.020 to 0.035% by weight/volume of camphor;

0.020 to 0.075% by weight/volume of eucalyptol;

a sufficient amount of a pharmaceutically acceptable buffer to maintain the pH of the composition within the range of about 6.25 to 6.75; and QS water.

3. The composition of claim 1 wherein the aromatic alcohol is benzyl alcohol; the non-mercurial anti-microbial preservative is benzalkonium chloride; the moisturizing agent is propylene glycol; the antioxidant is disodium EDTA; and the surfactant is polysorbate 80.

4. The composition of claim 3 comprising:

| Ingredients | % Wt/Vol |
| --- | --- |
| Water USP purified | 80.0000 |
| Sodium phosphate monobasic | 0.5525 |
| Sodium phosphate dibasic | 0.0975 |
| Disodium EDTA | 0.0200 |
| Benzyl alcohol | 1.0000 |
| Benzalkonium chloride (17% solution) | 0.1177 |
| Propylene glycol USP | 3.5000 |
| Polysorbate 80 | 1.2500 |
| L-Menthol USP | 0.1750 |
| Camphor USP | 0.0300 |
| Eucalyptol | 0.0300 |
| Oxymetazoline hydrochloride USP | 0.0500 |
| Water USP purified | QS. |

5. The composition of claim 3 comprising:

| Ingredients | % Wt/Vol |
| --- | --- |
| Water USP purified | 80.0000 |
| Sodium phosphate monobasic | 0.5525 |
| Sodium phosphate dibasic | 0.0975 |
| Disodium EDTA | 0.0200 |
| Benzyl alcohol | 0.2500 |
| Benzalkonium chloride (17% solution) | 0.1177 |
| Propylene glycol | 1.5000 |
| Polysorbate 80 | 1.1500 |
| L-Menthol USP | 0.0900 |
| Camphor USP | 0.0300 |
| Eucalyptol | 0.0300 |
| Oxymetazoline hydrochloride USP | 0.0500 |
| Water USP purified | QS. |

6. The composition of claim 3 comprising:

| Ingredients | % Wt/Vol |
| --- | --- |
| Water USP purified | 80.0000 |
| Sodium phosphate monobasic | 0.5525 |
| Sodium phosphate dibasic | 0.0975 |
| Disodium EDTA | 0.0200 |
| Benzyl alcohol | 0.2500 |
| Benzalkonium chloride (17% solution) | 0.1177 |

-continued

| Ingredients | % Wt/Vol |
|---|---|
| Propylene glycol | 1.5000 |
| Polysorbate 80 (Tween 80) | 1.1500 |
| L-Menthol USP | 0.0400 |
| Camphor USP (Synthetic) | 0.0100 |
| Eucalyptol | 0.0100 |
| Oxymetazoline hydrochloride USP | 0.0500 |
| Water USP purified | QS. |

7. The composition of claim 3 comprising:

| Ingredients | % Wt/Vol |
|---|---|
| Water USP purified | 80.0000 |
| Sodium phosphate monobasic | 0.5525 |

-continued

| Ingredients | % Wt/Vol |
|---|---|
| Sodium phosphate dibasic | 0.0975 |
| Disodium EDTA | 0.0200 |
| Benzyl alcohol | 0.2500 |
| Benzalkonium chloride (17% solution) | 0.1177 |
| Propylene glycol USP | 1.5000 |
| Eucalyptol | 0.0300 |
| Oxymetazoline hydrochloride | 0.0500 |
| Water USP purified | QS. |

8. A method of treating nasal congestion which comprises administering to a nasal passage of a patient with nasal congestion an aqueous, nasal, decongestant composition of claim 1.

* * * * *

UNITED STATES PATENT AND TRADEMARK OFFICE
CERTIFICATE OF CORRECTION

PATENT NO. : 5,854,269
DATED : December 29, 1998
INVENTOR(S) : Joseph A. Haslwanter, Germantown; William Rencher, Cordova, both of Tenn.

It is certified that error appears in the above-identified patent and that said Letters Patent is hereby corrected as shown below:

On Title Page, beneath the entry,

"[22] PCT Filed: November 17, 1994", insert:

-- Related U.S. Application Data

[63] Continuation of Ser. No. 08/155,052, November 19, 1993, abandoned. --

Column 1, immediately after the title, insert the following paragraph:

-- The present application is the United States national application corresponding to International Application No. PCT/US 94/12945, filed November 17, 1994 and designating the United States, which PCT application is in turn a continuation of U.S. Application Serial No. 08/155,052, filed November 19, 1993, the benefit of which applications are claimed pursuant to the provisions of 35 U.S.C. 120, 363 and 365(C). --

Signed and Sealed this

Twentieth Day of July, 1999

*Attest:*

Q. TODD DICKINSON

*Attesting Officer*    *Acting Commissioner of Patents and Trademarks*

(12) EX PARTE REEXAMINATION CERTIFICATE (5898th)
United States Patent
Haslwanter et al.

(10) Number: US 5,854,269 C1
(45) Certificate Issued: Sep. 25, 2007

(54) NASAL SPRAY COMPOSITIONS

(75) Inventors: Joseph A. Haslwanter, Germantown, TN (US); William Rencher, Cordova, TN (US)

(73) Assignee: Schering-Plough Healthcare Products, Inc., Memphis, TN (US)

Reexamination Request:
No. 90/007,442, Feb. 25, 2005

Reexamination Certificate for:
Patent No.: 5,854,269
Issued: Dec. 29, 1998
Appl. No.: 08/640,767
Filed: Aug. 5, 1996

Certificate of Correction issued Jul. 20, 1999.

(22) PCT Filed: Nov. 17, 1994
(86) PCT No.: PCT/US94/12945
§ 371 (c)(1),
(2), (4) Date: Aug. 5, 1996
(87) PCT Pub. No.: WO95/13810
PCT Pub. Date: May 26, 1995

Related U.S. Application Data

(63) Continuation of application No. 08/155,052, filed on Nov. 19, 1993, now abandoned.

(51) Int. Cl.
*A61K 9/00* (2006.01)
*A61K 31/415* (2006.01)

(52) U.S. Cl. ...................................... 514/385
(58) Field of Classification Search ....................... None
See application file for complete search history.

(56) References Cited

U.S. PATENT DOCUMENTS 3,975,536 A * 8/1976 Stevenson et al. .......... 514/456
5,562,908 A * 10/1996 Geria ......................... 424/434

OTHER PUBLICATIONS

Claisen OG and Kvamme R. Pharm. Ind. 39, Nr. 7 (1977), pp. 726–730.*

Physician's Desk Reference For Nonprescription Drugs (PDR) 1990 Edition, p. 684.*

* cited by examiner

*Primary Examiner*—Evelyn Mei Huang

(57) ABSTRACT

An aqueous nasal decongestant composition containing oxymatazoline is disclosed which does not contain mercurial preservatives.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–8 are cancelled.

* * * * *